United States Patent [19]
Haskill et al.

[11] Patent Number: 6,087,178
[45] Date of Patent: Jul. 11, 2000

[54] METHOD FOR DOWN REGULATING CD4 EXPRESSION IN A T CELL

[75] Inventors: John Stephen Haskill, Chapel Hill, N.C.; Peter Ralph, Orinda, Calif.

[73] Assignee: Chiron Corporation, Emeryville, Calif.

[21] Appl. No.: 08/477,143

[22] Filed: Jun. 7, 1995

Related U.S. Application Data

[62] Division of application No. 08/425,232, Apr. 18, 1995, Pat. No. 5,872,095, which is a continuation of application No. 07/791,474, Nov. 8, 1991, abandoned, which is a continuation-in-part of application No. 07/594,827, Oct. 9, 1990, abandoned.

[51] Int. Cl.⁷ .............................. C12N 15/85; C12N 5/10; C12N 15/12
[52] U.S. Cl. .................. 435/455; 435/320.1; 435/372.2; 424/93.2
[58] Field of Search ............................... 435/69.1, 240.2, 435/320.1, 172.3, 455, 372.2; 424/93.2

[56] References Cited

U.S. PATENT DOCUMENTS

| | | | |
|---|---|---|---|
| 4,399,216 | 8/1983 | Axel et al. | 435/6 |
| 4,419,446 | 12/1983 | Howley et al. | 435/69.1 |
| 4,601,978 | 7/1986 | Karin | 435/69.1 |
| 4,656,134 | 4/1987 | Ringold | 435/69.1 |
| 5,075,222 | 12/1991 | Hannum et al. | 435/69.1 |
| 5,180,812 | 1/1993 | Dower et al. | 530/351 |
| 5,359,032 | 10/1994 | Dayer et al. | 530/350 |

FOREIGN PATENT DOCUMENTS

WO 89/11540  11/1989  WIPO .

OTHER PUBLICATIONS

Verma et al., Nature, vol. 389, pp. 239–242, Sep. 18, 1997.
Carter, et al., "Purification, cloning, expression and biological characterization of an interleukin–1 receptor antagonist protein," Nature 344:633–368 (Apr. 12, 1990).
Cominelli, et al., "Interleukin 1 (IL–1) Gene Expression, Synthesis, and Effect of Specific IL–1 Receptor Blockade in Rabbit Immune Complex Colitis," J. Clin. Invest., 86:872–980 (Sep. 1990).
Dinarello, et al., "Multiple Biological Activities of Human Recombinant Interleukin 1," J. Clin. Invest., 77:1734–1739 (Jun. 1986).
Eisenberg, et al., "Primary structure and functional expression from complementary DNA of a human interleukin–1 receptor antagonist," Nature, 343:341–346, (Jan. 25, 1990).
Fanslow, et al., "Regulation of Alloreactivity in Vivo by a Soluble Form of the Interleukin–1 Receptor," Science, 248:739–742, (May 1990).
Gosset, et al., "Production of an Interleukin–1 Inhibitor Factor by Human Alveolar Macrophages from Normals and Allergic Asthmatic Patients," Am. Rev. Respir. Dis., 138:40–46 (1988).
Gershenwald, et al., "Interleukin 1 receptor blockade attenuates the host inflammatory response," Proc. Natl. Acad. Sci. USA, 87:4966–4970 (Jul. 1990).

Hannum, et al., "Interleukin–1 receptor antagonist activity of a human interleukin–1 inhibitor," Nature, 343:336–339 (Jan. 25, 1990).
Maliszewski, et al., "Cytokine Receptors and B Cell Functions–1. Recombinant Soluble Receptors Specifically Inhibit IL–1–and IL–4–Induced B Cell Activities in Vitro," The Journal of Immunology, 144:3028–3033, No.8 (Apr. 15, 1990).
Oppenheim, et al., "There is More Than One Interleukin 1," Immunology Today, Reviews, 7:45–56 No. 2 (1986).
Palaszynski, "Synthetic C–Terminal Peptide of IL–1 functions as a Binding Domain As Well As An Antagonist For The IL–1 Receptor," Biochemical and Biophysical Research Communications, 147:204–211, No. 1 (Aug. 31, 1987).
Seckinger, et al., "A Urine Inhibitor of Interleukin 1 Activity Affects Both Interleukin 1α and 1β But Not Tumor Necrosis Factor α," The Journal of Immunology, 139:1541–1545, No. 5 (Sep. 1, 1987).
Travis, J., "Mutant Gene Explains Some HIV Resistance," Science News, 150:103, (Aug. 17, 1996).
Liu, et al., "Homozygous Defect in HIV–1 Coreceptor Accounts for Resistance of Some Multiply–Exposed Individuals to HIV–1 Infection," Cell 86:367–377 (Aug. 8, 1996).
Simpson, et al., "Reduction of Experimental Canine Myocardial Reperfusion Injury by a Monoclonal Antibody (Anti– Mol, Anti–CD11b) That Inhibits Leukocyte Adhesion," J. Clin. Invest., 81:624–629 (Feb. 1988).
Dorland's Illustrated Medical Dictionary, 24th Ed., W.B. Saunders Company, Philadelphia, PA., p. 760, defining "ischemia," (1965).
Vedder, et al., "A Monoclonal Antibody to he Adherence–promoting Leukocyte Glycoprotein, CD18, Reduces Organ Injury and Improves Survival from Hemorrhagic Shock and Resuscitation in Rabbits," J. Clin. Invest., 81:939–944 (1988).
Cotran, et al., "Induction and Detection of a Human Endothelial Activation Antigen In Vivo," Brief Definitive Report, J. Exp. Med. 164: 661–666, (Aug. 1986).
Buchan, et al., "Interleukin–1 and tumor necrosis factor mRNA expression in rheumatoid arthritis: prolonged production of IL–1α," Clin. Exp. Immunol. 73:449–455 (Mar. 1988).

Primary Examiner—David Guzo
Attorney, Agent, or Firm—McAndrews, Held & Malloy; Robert P. Blackburn

[57] ABSTRACT

Medicaments and methods of using the same are disclosed for treating or preventing diseases resulting from undesirable cell adhesion of IL-1 receptor positive cells to biological materials, particular to endothelial cells, or autoimmune related diseases, preferably graft versus host disease, or IL-1 dependent cancers.

9 Claims, 2 Drawing Sheets

```
AGCTCCACCCTGGGAGGGACTGTGGCCCAGGTACTGCCCGGGTGCTACTT          -71

TATGGGCAGCAGCTCAGTTGAGTTAGAGTCTGGAAGACCTCAGA.AGACC          -22

MetAlaLeuGluThrIleCysArgPro
TCCTGTCCTATGAGGCCCTCCCCATGGCTTTAGAGACGATCTGCCGACCC           27
                                                             63
SerGlyArgLysSerSerLysMetGlnAlaPheArgIleTryAspValAs
TCTGGGAGAAAATCCAGCAAGATGCAAGCCTTCAGAATCTGGGATGTTAA           77 nGlnLysThrPheTyrLeuArgAsnAsnGlnLeuValAlaGlyTyrLeuG
CCAGAAGACCTTCTATCTGAGGAACAACCAACTAGTTGCTGGATACTTGC          127 lnGlyProAsnValAsnLeuGluGluLysIleAspValValProIleGlu
AAGGACCAAATGTCAATTTAGAAGAAAAGATAGATGTGGTACCCATTGAG          177

ProHisAlaLeuPheLeuGlyIleHisGlyGlyLysMetCysLeuSerCy
CCTCATGCTCTGTTCTTGGGAATCCATGGAGGGAAGATGTGCCTGTCCTG          227 sValLysSerGlyAspGluThrArgLeuGlnLeuGluAlaValAsnIleT
TGTCAAGTCTGGTGATGAGACCAGACTCCAGCTGGAGGCAGTTAACATCA          277 hrAspLeuSerGluAsnArgLysGlnAspLysArgPheAlaPheIleArg
CTGACCTGAGCGAGAACAGAAAGCAGGACAAGCGCTTCGCCTTCATCCGC          327

SerAspSerGlyProThrThrSerPheGluSerAlaAlaCysProGlyTr
TCAGACAGTGGCCCCACCACCAGTTTTGAGTCTGCCGCCTGCCCCGGTTG          377 pPheLeuCysThrAlaMetGluAlaAspGlnProValSerLeuThrAsnM
GTTCCTCTGCACAGCGATGGAAGCTGACCAGCCCGTCAGCCTCACCAATA          427 etProAspGluGlyValMetValThrLysPheTyrPheGlnGluAspGlu
TGCCTGACGAAGGCGTCATGGTCACCAAATTCTACTTCCAGGAGGACGAG          477

TAG                                                         480
```

METHOD FOR DOWN REGULATING CD4 EXPRESSION IN A T CELL

This application is a divisional of U.S. Ser. No. 08/425,232, filed Apr. 18, 1995, now U.S. Pat. No. 5,872,095; which is a continuation of U.S. Ser. No. 07/791,474, filed Nov. 8, 1991, now abandoned; which is a continuation-in-part of U.S. Ser. No. 07/594,827, filed Oct. 9, 1990, now abandoned.

FIELD OF THE INVENTION

This invention is in the area of medicinal chemistry, and presents medically useful compositions consisting of IL-1 receptor antagonists that have prophylactic or therapeutic applications for treating a variety of diseases including endothelial cell associated diseases, autoimmune related diseases, and cancer.

BACKGROUND OF THE INVENTION

Cytokines are small molecular weight proteins that have a myriad of normal biological functions as well as being associated with various diseases. For example, the cytokines interleukin-1 (IL-1) and tumor necrosis factor (TNF) have been demonstrated to have multiple biological activities with the two prominent being fever production and leukocyte activation. Moreover, both cytokines, alone or in combination, cause a shock state in animals that hemodynamically and hematologically is characteristic of septic shock in man caused by bacterial infection. TNF, in addition, has recently been shown to be involved in initiating the expression of human immunodeficiency virus in human cells that carry latent virus. Folks et al., 1989, *PNAS(USA)*, 86:2365. TNF and IL-1 also play a role in various autoimmune diseases, particularly arthritis. Duff, et al., 1987, *International Conference on Tumor Necrosis Factor and Related Cytotoxins*, 175:10.

Endothelial cell injury, or injury to the vascular system, can occur as a result of a number of disease in which there appears to be cytokine involvement. For example, ischemia-related injury to either cells, tissues or organs is responsible for many significant clinical disorders, including stroke, vascular disease, organ transplantation, and myocardial infarction. Leukocytes, particularly, neutrophils or monocytes, are thought to be the primary causative agent and have been shown to cause extensive vascular tissue damage arising as a result of the release of oxygen-derived free radicals, as well as proteases and phospholipases from the leukocytes at the site of injury. Harlan, J. M., 1987, *Acta. Med. Scand. Suppl.*, 715:123; Weiss, S., 1989, *New England J. of Med.*, 320:365. Cytokines are thought to be chemotactic agents for leukocytes and may be involved in attracting them to the site of tissue injury. Additionally, other studies have shown that cytokines are involved in causing leukocytes to adhere to the vascular endothelial cell layer which sets the stage for the release of noxious chemicals that cause vascular tissue damage.

Further evidence for the role of leukocytes in disease comes from studies which have shown that animals depleted of peripheral blood leukocytes show significantly reduced damage from myocardial ischemia and reperfusion. Further, reperfusion injury can be minimized by in vivo administration of monoclonal antibody to an adhesion protein present on leukocytes, termed MAC-1 (discussed more below). Finally, a rabbit model of hemorrhagic shock and resuscitation reveals that monoclonal antibodies against the β subunit of MAC-1 exhibited a protective effect to liver and the asternal intestinal track. Simpson, et l., 1988, *J. of Clinical Invest.*, 81:624; Vedder, N. and Harlan, J., 1988, *J. of Clinical Invest.*, 81:676.

The foregoing studies suggests significant therapeutic value for reagents that block the adhesion of leukocytes in controlling tissue and organ injury resulting from a number of disease situations including myocardial infarction, hemorrhagic shock, and other events that cause ischemia that are followed by reestablishing normal circulatory blood flow.

The initial event that leads to leukocyte, particularly neutrophil, damage of endothelial cells is the adhesion of neutrophils to the endothelial cell surface. In significant part this is mediated by cellular adhesion molecules associated with the neutrophils that cause them to bind to the endothelial cell surface. The neutrophil adhesion molecules bind to a molecule on the surface of endothelial cells termed ICAM-1 (Intercellular Adhesion Molecule 1). ICAM-1 is induced by one of several cytokines, including IL-1 and TNF. To date, a partial list of the adhesion molecules that have been identified that are involved in this reaction are lymphocyte function-associated antigen-1 (LFA-1), macrophage antigen-1 (MAC-1), also termed MO-1, OKM-1 and complement receptor type-3 (CR-3), and p150,95, also termed complement receptor type-4 (CR-4) and Leu M-5. These molecules collectively have been termed the LFA-1 family, leukocyte adhesion proteins, leuCAM, and leukocyte integrins. All three molecules are $\alpha$-$\beta$ heterodimers. The $\beta$ subunit is identical in the three molecules, while the $\alpha$ subunit differs. Kurzinger, K., and Springer, T. A., 1982, *J. of Biol. Chem.*, 257:12412; Sanchez-Madrid, F., et al., 1983, *J. Exp. Med.*, 158:1785; Trowbridge, I. S., and Omary, M. B., 1981, *PNAS (USA)*, 78:3039. Studies have shown the common $\beta$ subunit to play the predominant role in the adhesion-related functions of these molecules. Recently the cDNA clone that encodes the $\beta$ subunit of human LFA-1, MAC-1, and p150,95 has been isolated. Kishimoto, T., et al., 1987, *Cell*, 48:681; and Law, S. K. A. et al., 1987, *EMBO J.*, 6:915–919.

Studies have implicated the leukocyte integrins in cellular adhesion events. For example, LFA-1 is involved in antigen-dependent and antigen-independent interactions of immune cells. Springer, T. A., et al., 1987, *Annual Review Immun.*, 5:223; Martz, E., 1986, *Hum. Immunology*, 18:3. Most telling are studies utilizing a monoclonal antibody to LFA-1, which have revealed that binding to LFA-1 by monoclonal antibody partially or totally inhibits T lymphocyte adherence to endothelial cells (Mentzer, S. J., et al. 1986, *J. of Cell Physiol.*, 126:285), fibroblasts (Dustin, N. L., et al., 1986, *J. of Immun.*, 137:245), epidermal keratinocytes (Dustin, N. L., et al., 1988, *J. of SubBiology*, 107:321), and hepatocytes (Roos, E., and Roossien, F., 1987, *J. of SubBiology*, 105:553). Additionally, MAC-1 has been shown to be involved in macrophage binding to *Leishmania Promastigotes*, *E. coli*, and *Histoplasma Capsulatum*. Mosser, D. and Edelson, P., 1985, *J. of Immun.*, 135:2785; Wright, S. and Jong, M., 1986, *J. of Exp Med.*, 164:1876; Bullock, W. and Wright, S., 1987, *J. of Exp. Med.*, 165:195. Other studies have shown that MAC-1 is involved in neutrophil and monocyte chemotaxis, as well as adherence to glass and plastic surfaces, and to endothelial and epithelial cell monolayers. p150,95 is reported to be significantly involved in peripheral blood monocyte adhesion to substrates and endothelial cells, phagocytosis of latex particles, and chemotaxis. Keizer, et al., 1987, *Eur. J. of Immun.*, 17:1317; te Velde, A., et al., 1987, *Immunology*, 61:261. Further, studies using a monoclonal antibody that is directed to p150,95 have shown it to be utilized in conjugate formation by cytotoxic T lymphocytes.

There are two forms of IL-1:IL-1 α and IL-1 β. Although these molecules share limited sequence homology they have similar biological activity. Dinarello, C. A., et al., 1986, *Journal Clinical Invest.*, 77:1734. Both molecules have molecular weights of about 17.5 kD, and are produced from a precursor molecule with a molecular weight of about 31 kD.

Because IL-1 has pleiotropic biological activities many of which adversely affect the organism, it would be expected that the molecule must be tightly regulated if it is not to be injurious. Indeed, there are several reports of IL-1 inhibitors that regulate the action of IL-1. IL-1 inhibitory activity has been reported in monocyte conditioned medium, wherein the monocytes are grown on adherent immune complexes. Arend, W. P., et al., 1985, *Journal of Immun.*, 134:3868. Additionally, an inhibitor has been reported to be present in urine. Seckinger, P., et al., 1987, *Journal of Immun.*, 139:1546. Lastly, two protein inhibitors, purified and cloned, that have interleukin-1 receptor antagonist activity have been reported. Hannum, et al., 1990, *Nature*, 343:336; Eisenberg, S., et al., 1990, *Nature*, 343:341; and Haskill, S., et al., U.S. Ser. No. 517,276, filed May 1, 1990; Carter, D. et al., 1990, *Nature*, 344:633.

It is thought that the IL-1 inhibitor present in urine, and which has been partially purified and characterized by Seckinger, P. et al., supra and Seckinger, P., et al., 1987, *Journal of Immun.*, 139:1541 is similar, if not identical to the cloned IL-1 receptor antagonist reported by Eisenberg, S., et al., supra; and Carter, D., et al., 1990, *Nature*, 344:633.

As alluded to above, the leukocyte integrins bind to the cell surface protein, ICAM-1, which in turn is induced by one or more cytokines, particularly IL-1 or TNF. Thus, it will be appreciated that an effective modality for preventing endothelial cell injury that occurs during various diseases would be to interfere with the induction of ICAM-1 via molecules that prevent or interfere with the activity of IL-1, TNF or other molecules that induce ICAM-1.

IL-1 also plays a role in various autoimmune or autoimmune related diseases (Duff, et al., 1987, International Conference on Tumor Necrosis Factor and Related Cytotoxins, 175:10), particularly graft-versus-host rejection involving bone marrow transplants. This is attributable, at least in part, to IL-1 induction of IL-2 production by T-cells which in turn promotes the growth of additional T-cells. Thus, the graft from a donor contains a significant number of immunocompetent lymphoid cells that can mount an effective destructive reaction against host cells. Bone marrow transplants are often employed to treat various malignant diseases, including leukemia. Generally this involves immunologically crippling the leukemic patient, and then transplanting bone marrow from a donor. Unless the lymphoid cells in the donor marrow are suppressed they can react against recipient tissue antigens, often with dire consequences.

A variety of drugs, and antisera to lymphoid cells are used to treat graft versus host disease. Particularly useful drugs are corticosteroids, othiopirne, and cyclosporine. In addition, various monoclonal antibodies, alone or when coupled to a cytotoxic agent are available for ridding the donor marrow of lymphoid cells. P. S. Russell et al., *Annual Review Medicine*. 35:63 (1984). These drugs, however, have significant untoward side effects.

Finally, it has recently been suggested that IL-1 is an autocrine and paracrine growth factor for particular cancers. Tsai, 1987, *J. Natl. Cancer Inst.*, 79:77. Thus, compounds that interfere with the cancer growth activity of IL-1 may be effective chemotherapeutics.

SUMMARY OF THE INVENTION

The invention presented herein describes applications of medicaments consisting of IL-1 receptor antagonists for preventing or treating diseases, as well as methods for preventing or treating diseases using IL-1 receptor antagonists in appropriate assay formats.

A second aspect of the invention presents applications of medicaments consisting of IL-1 receptor antagonists for preventing or treating diseases caused by the undesirable adhesion of leukocytes to endothelial cells, or for preventing or treating autoimmune related diseases, preferably graft-versus-host disease, or for treating IL-1 dependent cancers.

A third aspect of the invention presents applications of medicaments consisting of IL-1 receptor antagonists for preventing or treating diseases that result in endothelial cell damage, preferably ischemia-related diseases, including stroke, vascular disease, organ transplantation, and myocardial infarction.

A fourth aspect of the invention is the description of medical uses of intracellular IL-1 receptor antagonists for preventing or treating diseases that result in endothelial cell damage, preferably ischemia-related diseases, including stroke, vascular disease, organ transplantation, and myocardial infarction, or for preventing or treating autoimmune related diseases, preferably graft-versus-host disease, or for treating Il-1 dependent cancers.

A fifth aspect of the invention is a method of treating or preventing HIV infection in a host consisting of incorporating into host cells a nucleotide sequence that encodes IL-1 receptor antagonist activity.

These and other aspects of the invention will be apparent upon a full consideration of the invention as presented below.

BRIEF DESCRIPTION OF THE DRAWINGS

Table 1 shows the effect of cellular COS cell lysates prepared from COS cells that were mock transfected, transfected with the vector, SRα, with or without the IL-1 receptor antagonist DNA sequence, or containing the sequence in the wrong orientation, or with a vector that encodes IL-2.

Table 2 shows the effect of COS cell lysates on IL-2 production from LBRM-33 cells when the lysates are prepared from mock transfected cells, cells containing the vector, SRα, that lacks the IL-1 receptor antagonist DNA sequence, the SRα vector that contains the IL-1 receptor antagonist DNA sequence, but in the wrong orientation, and the SRα vector that contains the IL-1 DNA sequence in the proper orientation.

Table 3 shows the effect of COS cell lysates on the inhibition of prostaglandin production in IL-1 inducible fibroblasts. COS cell lysates were prepared from COS cells that were mock transfected, transfected with the vector, SRα, with or without the IL-1 receptor antagonist DNA sequence, or containing the sequence in the wrong orientation.

DETAILED DESCRIPTION OF THE INVENTION

The invention described herein draws on previously published work. By way of example, such work consists of scientific papers, patents or pending patent applications. All of these publications and applications, cited previously or below, are hereby incorporated by reference.

The instant invention is composed of several unique methods and compositions. Each aspect of the invention will now be discussed separately.

"IL-1 Receptor Antagonist" refers to virtually any molecule that interferes with, or prevents the binding of IL-1 to its receptor. By way of example, and not by way of limitation, such antagonist are exemplified herein by two protein molecules that have been purified and cloned, that have interleukin-1 receptor antagonist activity have been reported. Hannum, et al., 1990, *Nature*, 343:336; Eisenberg, S., et al., 1990, *Nature,* 343:341; and Haskill, S., et al., U.S. Ser. No. 517,276, filed May 1, 1990. Other IL-1 Receptor Antagonist would include antibody that binds to, and interferes with or prevents the binding of IL-1 to its receptor. By antibody is intended any molecule that would have an anti-IL-1 receptor antibody combining site and would include, of course, polyclonal or monoclonal antibody or fragments derived therefrom, and molecules that have antibody binding activity made by recombinant methods. Monoclonal antibody to the IL-1 receptor may be produced using the general procedures described by Kohler, G. and Milstein, C., 1975, *Nature*, 256:495, which have been modified over the years as is known in the art. Antibody that binds to the receptor and interferes with IL-1 binding are readily identified using competition binding assays known in the art.

It is important to note that the definition of IL-1 receptor antagonist is not meant to exclude such molecules from having other properties. For example, it has been surprisingly discovered that in some instances such molecules have agonist activity as well. This is shown by the results in Example 6, wherein the intracellular IL-1 receptor antagonist down regulates CD4 expression on a T-cell line despite such cells not expressing detectible levels of IL-1

"Cells" or "recombinant host" or "host cells" are often used interchangeably as will be clear from the context. These terms include the immediate subject cell, and, of course, the progeny thereof. It is understood that not all progeny are exactly identical to the parental cell, due to chance mutations or differences in environment.

As used herein the term "transformed" in describing host cell cultures denotes a cell that has been genetically engineered to produce a heterologous protein that possesses the activity of the native protein. Examples of transformed cells are described in the examples of this application. Bacteria are preferred microorganisms for producing the protein. Synthetic protein may also be made by suitably transformed yeast and mammalian host cells.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein, the term "pharmaceutically acceptable" refers to a carrier medium which does not interfere with the effectiveness of the biological activity of the active ingredients and which is not toxic to the hosts to which it is administered. The administration(s) may take place by any suitable technique, including subcutaneous and parenteral administration, preferably parenteral. Examples of parenteral administration include intravenous, intraarterial, intramuscular, and intraperitoneal, with intravenous being preferred.

As used herein, the term "prophylactic or therapeutic" treatment refers to administration to the host of the cytokine inhibitor either before or after infection or cancer detection. If the cytokine inhibitor is administered prior to exposure to the infecting agent, the treatment is prophylactic (i.e., it protects the host against infection), whereas if administered after infection or initiation of cancer, the treatment is therapeutic (i.e., it combats the existing infection or cancer).

I. IL-1 Receptor Antagonists

Figure 1:
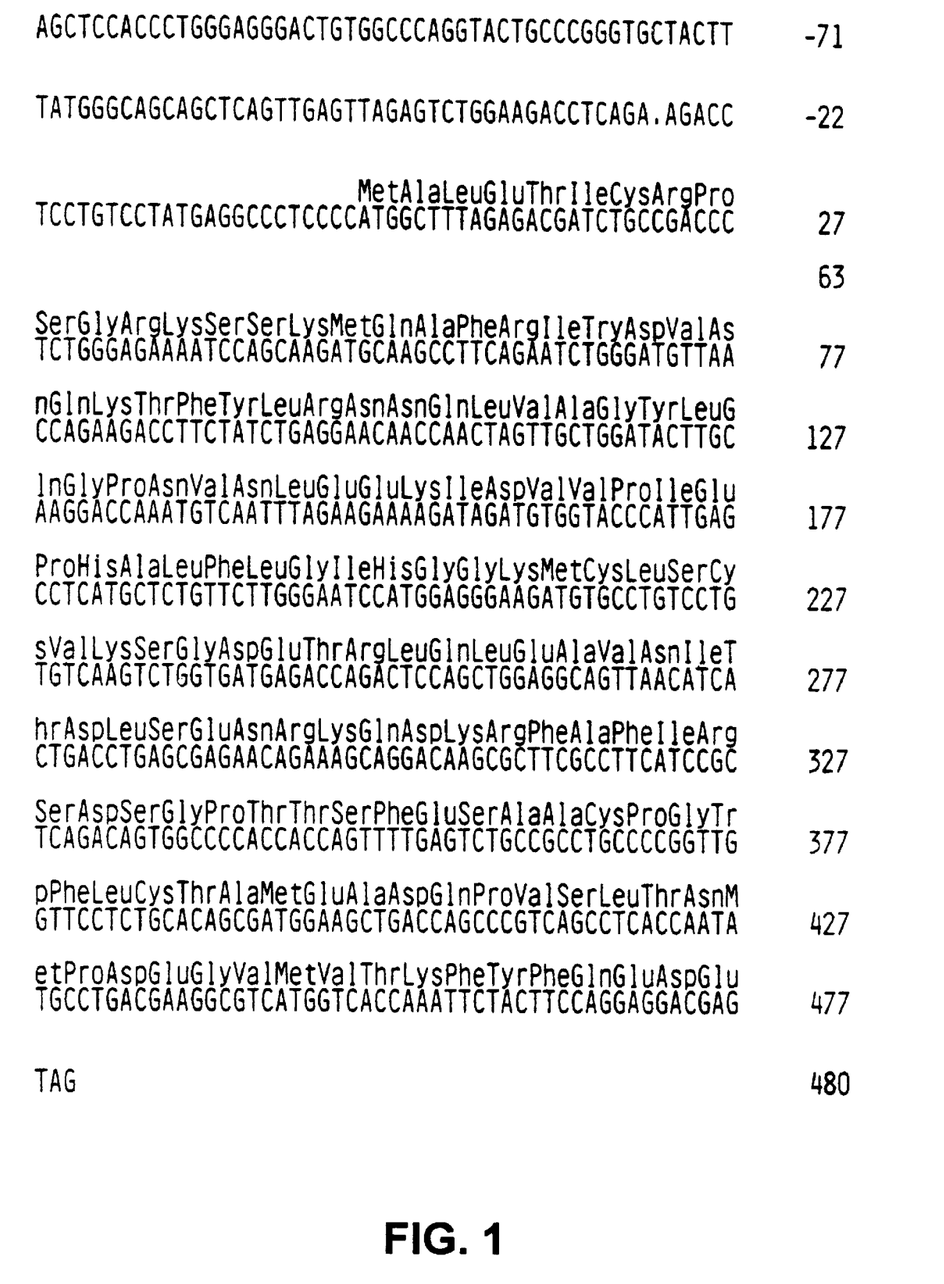
FIG. 1 discloses a DNA sequence (SEQ ID NO: 1) and the corresponding amino acid sequence (SEQ ID NO: 2) of the intracellular IL-1 receptor antagonist encoded thereby.

A. Isolated/Cloned Protein Antagonist:

FIG. 1 shows the amino acid sequence of the intracellular form of the human IL-1 receptor antagonist (SEQ ID NO: 2). The cDNA sequence that encodes the molecule has been described in U.S. Pat. Ser. No. 517,276, filed May 1, 1990, now U.S. Pat. No. 5,455,330, and in Haskill, S. et al., *PNAS*, in press. The cDNA sequence (SEQ ID NO: 1) is on deposit with the American Type Culture Collection (ATCC), 10801 University Boulevard, Manassas Va. 20110-2209 and the Cetus Microbial Culture Collection and has ATCC Accession No. 68449 and CMCC No. 3827, respectively. A secreted form of the intracellular IL-1 receptor antagonist is described by Hannum, et al., 1990, *Nature*, 343:336; Eisenberg, S., et al., 1990, *Nature*, 343:341. Carter et al., supra.

The IL-1 receptor antagonist cDNA sequence (SEQ ID NO: 1) can be expressed in a number of expression systems, and in a wide variety of cell types. Procaryotes most frequently are represented by various strains of *E. coli*. However, other microbial strains may also be used, such as bacilli, for example, *Bacillus subtilis*, various species of *Pseudomonas*, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., 1977, *Gene* 2:95. pBR322 contains genes for ampicillin and tetracycline resistance, and thus provides additional markers which can be either retained or destroyed in constructing the desired vector. Commonly used procaryotic control sequences, which are defined herein to include promoters for transcription initiation, optionally with an operator, along with ribosome binding site sequences, include such commonly used promoters. as the beta-lactamase (penicillinase) and lactose (lac) promoter systems (Chang et al., 1977, *Nature* 198:1056), the tryptophan (trp) promoter system (Goeddel et al., 1980, *Nucleic Acids Res*. 8:4057) and the lambda derived $P_L$ promoter (Shimatake et al., 1981, *Nature* 292:128), and N-gene ribosome binding site, which has been made useful as a portable control cassette, U.S. Pat. No. 4,711,845, issued Dec. 8, 1987, and incorporated herein by reference in its entirety, which comprises a first DNA sequence that is the $P_L$ promoter operably linked to a second DNA sequence corresponding to the $N_{RBS}$ upstream of a third DNA sequence having at least one restriction site that permits cleavage within 6 bp 3' of the $N_{BRS}$ sequence. U.S. Pat. No. 4,666,848, issued May 19, 1987, and incorporated herein by reference in its entirety discloses additional vectors with enhanced expression capabilities. Also useful is the phosphatase A (phoA) system described by Chang et al., in European Patent Publication No. 196,864, published Oct. 8, 1986, incorporated herein by reference. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, 1983, *Meth. Enz.*, 101:307; U.S. Pat. No. 4,803,164, incorporated herein by reference in its entirety), other plasmid vectors suitable for yeast expression are known (see, for example, Stinchcomb et al., 1979, *Nature* 282:39, Tschempe et al., 1980, Gene 10:157 and Clarke et al., 1983, *Meth. Enz.* 101:300). Control sequences for yeast vectors include promoters for the synthesis of glycolytic enzymes (Hess et al., 1968, *J. Adv. Enzyme. Req.* 7:149; Holland et al., 1978, *Biochemistry* 17:4900).

Additional promoters useful in yeast host microorganisms and known in the art include the promoter for 3-phosphoglycerate kinase (Hitzeman et al., 1980, *J. Biol. Chem.* 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, supra ).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., 1981, *J. Biol. Chem.* 256:1385) or the LEU2 gene obtained form YEp13 (Broach et al., 1978, *Gene* 8:121); however, any vector containing a yeast compatible promoter, origin of replication and other control sequences is suitable.

It is also, of course, possible to express genes encoding proteins in eucaryotic host cell cultures derived from multicellular organisms. See, for example, *Tissue Culture* Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature*, 273:113) viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,446, entitled "Recombinant DNA Process Utilizing A Papilloma Virus DNA As A Vector," which issued Dec. 06, 1983, and is incorporated herein by reference in its entirety. A modification of this system is described in U.S. Pat. No. 4,601,978, entitled "Mammalian Metallothionein Promoter System," which issued Jul. 22, 1986, and is incorporated herein by reference in its entirety. General aspects of mammalian cell host system transformations have been described by Axel in U.S. Pat. No. 4,399, 216, issued Aug. 16, 1983. Also useful is gene amplification in eucaryotic cells as described by Ringold in U.S. Pat. No. 4,656,134, entitled "Gene Amplification In Eukaryotic Cells," which issued Apr. 7, 1987, incorporated herein by reference in its entirety. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes.

Plant cells are also now available as hosts, and control sequence compatible with plant cells such as the nopaline synthase promoter and polyadenylation signal sequences (Depicker et al., 1982, *J. Mol. Appl. Gen.*, 1:561) are available. Additionally, methods and vectors for transformation of plant cells have been disclosed in PCT Publication No. WO 85/04899, published Nov. 7, 1985, and incorporated herein by reference in its entirety.

It will be appreciated by those skilled in the art that although the precise chemical structure of the IL-1 receptor antagonist is shown in FIG. 1, and conservative amino acid changes or deletions or in the case of antibody antagonists are readily determined using known sequencing methods, the primary amino acid sequence of the protein may be augmented by derivatization using sugar moieties (glycosylation) or by other supplementary molecules such as lipids, phosphate, acetyl groups and the like, as well as by conjugation with saccharides, polyethylene glycols (PEGs) and polyoxyethylene glycols (POGs). Such modifications are included in the definition of peptide herein so long as the activity of the peptide, as defined above, is not destroyed. It is expected, of course, that such modifications may quantitatively or qualitatively affect the activity, either by enhancing or diminishing the activity of the protein in the various assays.

B. Antibody IL-1 Receptor Antagonists:

Procedures for producing antibody, polyclonal or monoclonal, are well known in the art and may be adapted to produce IL-1 receptor antibody that binds to the receptor and prevents or interferes with IL-1 binding. The methods for generating monoclonal antibody are described by Kohler, G. and Milstein, C., 1975, *Nature*, 256:495. These initial studies involved fusing murine lymphocytes and drug selectable plasmacytomas to produce hybridomas. Subsequently, the technique has been applied to produce hybrid cell lines that secrete human monoclonal antibodies. The latter procedures are generally described in Abrams, P., 1986, *Methods in Enzymology*, 121:107, but other modifications are known to those skilled in the art. Regardless of whether murine or human antibody is produced, the antibody secreting cells are combined with the fusion partner and the cells fused with a suitable fusing agent, preferably polyethylene glycol, and more preferably polyethylene glycol 1000. The latter is added to a cell pellet containing the antibody secreting cells and the fusion partner in small amounts over a short period of time accompanied with gentle agitation. After the addition of the fusing agent, the cell mixture is washed to remove the fusing agent and any cellular debris, and the cell mixture consisting of fused and unfused cells seeded into appropriate cell culture chambers containing selective growth media. After a period of several weeks, hybrid cells are apparent, and may be identified as to antibody production and subcloned to ensure the availability of a stable hybrid cell line.

The preferred antibody is human monoclonal antibody which can be prepared from lymphocytes sensitized with IL-1 receptor, or with cells that bear the same, either in vivo or in vitro by immortalization of antibody-producing hybrid cell lines, thereby making available a permanent source of the desired antibody. In vivo immunization techniques are well known in the art, while in vitro techniques are generally described by Luben, R. and Mohler, M., 1980, *Molecular Immunology*, 17:635, Reading, C. *Methods in Enzymology*, 121 (Part One):18, or Voss, B., 1986, *Methods in Enzymology*, 121:27. A number of in vitro immunization systems have been shown to be effective for sensitizing human B-cells. Reading, C., 1982, *J. of Immun. Methods*, 53:261.

Sensitized lymphocytes can be immortalized by viral transformation. The preferred viral transformation technique for human lymphocytes involves the use of Epstein-barr virus. The virus is capable of transforming human B-cells, and has been used to generate human monoclonal antibodies. Crawford, D. et al., 1983, *J. of General Virology*, 64:697; Kozbor, V. and Roder, J., 1983, *J. Immun. Today*, 4:72.

Another procedure whereby sensitized lymphocytes may be immortalized consist of a combination of the above two techniques, that is viral transformation and cell fusion. The preferred combination consist of transforming antibody secreting cells with Epstein-barr virus, and subsequently fusing the transformed cells to a suitable fusion partner. The fusion partner may be a mouse myeloma cell line, a heteromyeloma line, or a human myeloma line, or other immortalized cell line. PCT Patent Application No. 81/00957; Schlom et al., 1980, *PNAS (USA)*, 77:6841; Croce et al., 1980, *Nature*, 288:488. The preferred fusion partner is a mouse-human hetero-hybrid, and more preferred is the cell line designated F3B6. This cell line is on deposit with the American Type Culture Collection, Accession No. HB8785. It was deposited Apr. 18, 1985. The procedures for generating F3B6 are described in European Patent Application, Publication No. 174,204.

Techniques applicable to the use of Epstein-Barr virus transformation and the production of immortal antibody secreting cell lines are presented by Roder, J. et al., 1986, *Methods in Enzymology*, 121:140. Basically, the procedure consist of isolating Epstein-Barr virus from a suitable source, generally an infected cell line, and exposing the target antibody secreting cells to supernatants containing the virus. The cells are washed, and cultured in an appropriate cell culture medium. Subsequently, virally transformed cells present in the cell culture can be identified by the presence of the Epstein-Barr viral nuclear antigen, and transformed antibody secreting cells can be identified using standard methods known in the art.

The hybridoma cells may be grown in appropriate cell culture media, and the supernatant screened for the presence of monoclonal antibody that prevents or interferes with binding of IL-1 to its receptor using, for example, an enzyme linked immunosorbent assay (ELISA). The latter is described by Engvall, E., 1977, *Med. Biol.*, 55:193. Basically, the procedure consist of coating flat-bottom 96 well microtitre plates with the appropriate source of IL-1 receptor antigen, preferably either purified IL-1 receptor or cells that carry the receptor, reacting the antigen with cell culture supernatant, removing the supernatant and then revealing the presence of antibody using a suitable second antibody that has been labelled with a reporter group. It is well known in the art that the reporter group is preferably a radioactive tracer or a fluorescent molecule. Procedures for isolating IL-1 receptor are described in European patent application, Publication No. 318,296, to Dower, S. K. et al., published May 31, 1989.

Those hybridomas that initially give a positive signal and therefore secrete antibody that bindings to the receptor are retested in the presence of IL-1 to determine if the antibody has IL-1 receptor antagonist activity. This assay is preferably conducted using labelled IL-1 and measuring a reduction in IL-1 binding to the receptor in the presence of antibody.

It will be apparent to those skilled in the art that while the preferred embodiment of the instant invention is anti-IL-1 receptor monoclonal antibody, singly or in combination, that the antibody(s) may be altered and still maintain biological activity. Thus, encompassed within the scope of the invention is antibody modified by reduction to various size fragments, such as F(ab')$_2$, Fab, Fv, or the like. Also, the hybrid cell lines that produce the antibody may be considered to be a source of the DNA that encodes the desired antibody, which may be isolated and transferred to cells by known genetic techniques to produce genetically engineered antibody. An example of the latter would be the production of single chain antibody having the antibody combining site of the hybridomas described herein. Single chain antibody is described in U.S. Pat. No. 4,704,692, or in U.S. Pat. No. 4,946,778. A second example of genetically engineered antibody is recombinant, or chimeric antibody. Methods for producing recombinant antibody are shown in U.S. Pat. No. 4,816,567, inventor Cabilly, et al.; Japanese patent application, Serial No. 84169370, filed Aug. 15, 1984; U.S. patent application, Ser. No. 644,473, filed Aug. 27, 1984, now abandoned; British patent application 8422238, filed on Sep. 3, 1984; Japanese patent application, No. 85239543, filed Oct. 28, 1985; U.S. patent application, Ser. No. 793,980 on Nov. 1, 1985, now abandoned; U.S. patent application, Ser. No. 77,528, filed Jul. 24, 1987, now abandoned. Also, British patent application, No. 867679, filed Mar. 27, 1986 describes methods for producing an altered antibody in which at least parts of the complementary determining regions (CDRs) in the light or heavy chain variable domains have been replaced by analogous parts of CDRs from an antibody of different specificity. Using the procedures described therein it is feasible to construct recombinant antibody having the CDR region of one species grafted onto antibody from a second species that has its CDR region replaced. The preferred embodiment in this instance is a murine anti-L- 1 receptor antibody CDR region that replaces the CDR region of human antibody. Hybrid cells produced by fusing antibody secreting cells and an appropriate fusion partner, or Epstein-Barr virus transformed cells that produce the desired antibody can be identified using convenient immunochemical screening techniques.

Regardless of whether the antibody being screened is monoclonal, recombinant, single chain etc., the assay described above may be employed to identify IL-1 receptor antagonists.

C. Formulation of IL-1 Receptor Antagonists:

It will be appreciated by those skilled in the art that the IL-1 receptor antagonists described herein can be administered to mammals, including humans, either alone or in combination with other anti-inflammatory agents, or they may be combined with various pharmaceutically acceptable diluents or carriers. Such are widely known to those skilled in the art and are formulated according to standard pharmaceutical practices.

Exemplary diluents include physiologic saline, or buffered saline, as well as Ringer's and dextrose injection fluid, and dextrose saline and lactated Ringer's injection or diluent solutions containing additional therapeutic agents, preferably antibiotics or antibodies known to be efficacious in the treatment of inflammatory conditions.

II. Leukocyte Preparation/Labelling

Leukocyte adherence can be measured using several assays known in the art, and the preferred assay is described by Charo, et al., 1985, *Blood*, 65:473. Briefly, the assay consists of labelling leukocytes with an appropriate label, incubating the leukocytes with endothelial cells and determining the number of leukocytes that adhere. Preferably the cells are labelled with a gamma ray emitting isotope and the preferred labels are $^{111}$Indium-oxide or $^{51}$chromium.

Leukocytes may be isolated from human donors using standard techniques. This generally consists of isolating blood in a physiologically balanced salt solution containing an appropriate anticoagulant, and separating the leukocytes by an appropriate separation step, preferably on Ficoll-Hypaque gradients. Contaminating erythrocytes can be removed by hypotonic lysis. The resulting leukocytes are suspended in a physiologically buffered solution, pH 7.4. The preferred physiological buffered solution is Hank's balanced salt solution that is calcium and magnesium free.

The isolated leukocytes can then be labelled by incubating them for an appropriate time, generally 15 minutes, with the desired radioisotope at a predetermined concentration. The radiolabelled cells are washed to remove unincorporated label, and then suspended in an appropriate solution to perform the adhesion assay described below.

III. Endothelial Cell Preparation/Culture

Endothelial cells can be prepared from a number of sources and by several techniques known in the art. Preferably they are obtained from human umbilical veins using the procedure of Charo et al., above. Generally, endothelial cells are isolated by enzymatic digestion of the umbilical veins using, preferably, collagenase as described by Jaffe, E. A., et al., 1973, *J. of Clin. Invest*, 52:2745. The cells are grown on an appropriate tissue culture substratum, preferably gelatine-coated surfaces.

The endothelial cells may be grown in a variety of tissue culture media containing appropriate supplements such as an appropriate concentration of fetal calf serum, and other supplements/additives routinely utilized by those skilled in this art that are recognized as being favorable for endothelial cells. The endothelial cells may be passaged with a dilute solution of an appropriate protease, and if desired a metal ion chelator. Preferably a solution consisting of 0.05 to 0.25% trypsin and 0.02% EDTA is used To ensure that the cells are indeed endothelial cells, they are tested by immunofluorescence for Factor VIII antigen, a known endothelial cell marker.

IV. Leukocyte/Endothelial Cell Adhesion Assay

Leukocyte adherence to endothelial cell monolayers may be determined as follows. Early passage endothelial cells, generally not beyond the fifth passage, are cultured on an appropriate substratum and in a suitable cell culture medium. The culture substratum is preferably pre-coated with an appropriate substance that enhances the adherence of the endothelial cells. Several such substances are known including fibronectin, poly-L-lysine, gelatin and laminin. Fibronectin is preferred. An appropriate culture substratum is a 96-well micro titer plate, and a suitable medium is Medium 199 containing fetal calf serum and other supplements known to be beneficial for the growth and maintenance of endothelial cells that are well known to those skilled in the art. The endothelial cell monolayer is washed with a physiologically balanced salt solution containing a reduced amount of fetal calf serum, preferably 1%. The preferred solution is RPMI supplemented with 1% fetal calf serum. Prior to the adhesion step, endothelial cells and/or leukocytes are incubated with IL-1 to induce membrane adhesion molecules. Preferably 10 U/ml IL-1 β is added to the endothelial cells for 4 hours.

The endothelial cell monolayer containing added leukocytes preferably $^{111}$Indium monocytes are incubated for a time sufficient to permit maximum adherence of the leukocytes, and preferably this is conducted at 37° C. for 30 minutes in an appropriate cell culture atmosphere. Generally this would consist of incubating the cells for the assay period in 5% $CO_2$, 95% air, and 95% humidity. Next, non-adherent leukocytes are removed by any number of techniques known in the art, and the number of leukocytes adherent to the endothelial cell monolayers determined by measuring the amount of radioisotope associated with the endothelial cell monolayer. Controls are run that take into account basal binding, i.e., binding to endothelial cells not activated with IL-1.

In a typical experiment run in quadruplicate, the assay is highly reliable, giving standard deviations less than 10%, and usually less than 5%, of mean values. Typically the results are expressed as the percent of leukocytes added to the endothelial cells that remain adherent after non-adherent cells have been removed.

Using the above assay, typically the IL-1 receptor antagonist is added over a range of concentrations and preferably at $10^{-4}$ M. This volume is then suitably diluted in an appropriate medium, preferably RPMI containing 1% fetal calf serum to give the desired final concentration to be tested.

The endothelial cells were activated with 10 U/ml of IL-1 β (Genzyme Corp.) for at least 4 hours in RPMI with 1% fetal calf serum prior to the addition of the leukocytes. IL-1 causes the induction of ICAM expression on endothelial surfaces which is a receptor for leukocyte integrin binding.

V. Determination of the Effectiveness of an IL-1 Receptor Antagonist in Graft Versus Host Disease Using Primary Mixed Lymphocyte and Phytohemagglutinin Assays The mixed lymphocyte response (MLR) and phytohemagglutinin A (PHA) assays are valuable for identifying immune suppressive molecules in vitro that are useful for treating graft-versus-host disease. The results obtained from these assays are generally predictive of their in vivo effectiveness.

The in vitro mixed lymphocyte assay is presently employed in the clinical setting as an indicator of histocompatibility, and is premised on the transformation of resting genetically dissimilar lymphocytes into cells which synthesize DNA and undergo proliferation. It has been demonstrated that incompatibility at the major histocompatibility complex is mainly responsible for this phenomenon.

A second assay widely used to study immune responsiveness is mitogenic stimulation of lymphocytes with mitogenic substances of plant origin. The most widely used mitogen molecule is PHA. Although PHA stimulates DNA synthesis non-specifically in a large number of lymphocytes, unlike true antigenic stimulation which causes mitogenesis of subpopulations of lymphocytes, the susceptibility of a patient's lymphocytes to PHA stimulation has been shown to correlate with the overall immune responsiveness of the patient.

Thus, it will be appreciated as to both the mixed lymphocyte and PHA assay that they are valuable for identifying immune suppressive molecules in vitro, and that the results obtained therefrom are generally predictive of their in vivo effectiveness.

In addition to the above immunosuppressive assays, a secondary mixed lymphocyte reaction assay may also be used. The secondary mixed lymphocyte assays differs from the primary mixed lymphocyte reaction assays in that they employ many more primed responder cells that are responsive to the primary stimulating cells. The presence of such responsive cells is a reflection of immunological memory in an ongoing immunological response. The protocol for carrying out a secondary mixed lymphocyte assay involves performing a primary lymphocyte assay as described above, and recovering viable cells about 9–10 days after the primary mixed lymphocyte reaction exhibits little or no cell proliferation. Generally between 10% to 50% of the original input cells are recovered in viable condition. These cells are then used in the secondary mixed lymphocyte reaction.

The procedure for carrying out a secondary mixed lymphocyte reaction is described by T. Meoen, *Immnunological Methods*, Eds I. Lefkoivits and B. Pernis, Economic Press, New York (1979). It will be appreciated that described therein is a method for carrying out secondary lymphocyte reactions using mouse cells, however such methods are generally applicable to performing secondary mixed lymphocyte reactions using human cells with modifications that are well known to those skilled in the art.

Using one or all of the above assays, the immune suppressive effectiveness of IL-1 receptor antagonists can be determined, and thus their use in treating graft versus host disease defined. The assays can be performed as is known in the art, and with or without added IL-1 receptor antagonists. The antagonists would be added to the assay reaction mixture at various concentrations to ascertain the concentration that is optimally effective.

Having described what the applicants believe their invention to be, the following examples are presented to illustrate the invention, and are not to be construed as limiting the scope of the invention. For example, variation in the source, type, or method of producing antibodies; different labels and/or signals; test supports of different materials and configurations; different immobilization methods may be employed without departing from the scope of the present invention.

EXAMPLE 1

Effect of IL-1 Receptor Antagonist on Monocyte Adhesion to Endothelial Cell Monolayers COS cell lysates containing IL-1 receptor antagonist were tested for their capacity to interfere with, or block adhesion of monocyte to human endothelial cell monolayers. A variety of controls were also run including a buffer control or performing the assay using lysates prepared from cells transfected with the vector, SRα, without the IL-1 receptor antagonist DNA sequence (SEQ ID NO: 1) or with the sequence in the wrong orientation. Also, the effects of IFN, and IL-2 were tested. COS cells were cultured in MEM (minimal essential medium) with high glucose, +10% FBS.

COS cell lysates were prepared from COS-7 cells that were transfected with plasmid DNA containing the PstI fragment, which contains all of the 5' untranslated, the complete open reading frame, and 60 based pairs of the 3' untranslated region. Transfection was achieved using the DEAE-dextran/chloroquine technique as described by Wong, G. G. et al., 1985, *Science*, 228:810. Three days subsequent to the transfection, the supernatant and cells were freeze thawed to obtain a culture lysate. Suitable dilutions of the lysate were employed in the experiments described below.

The endothelial cells were isolated from human umbilical cords by mild collagenase digestion. Collagenase was obtained from Worthington Corporation, Freehole, N.J., and the general procedure is described by Jaffe, E. A., et al., 1973, *J. of Clin. Invest.*, 52:2745. The cells obtained from collagenase digestion were grown on gelatin-coated flasks in cell culture medium consisting of medium 199 (Gibco, Grand Island, N.Y.) buffered with 25 mM Hepes. The media was supplemented with 20% fetal calf serum. The media also contained 60 $\mu$g/ml sodium heparin (Sigma Corporation, St. Louis, Mo.), 2 mM L-glutamine and 50 $\mu$g/ml of bovine hypothalamus extract. The bovine tissue was obtained from Pel Freeze, Rogers, Ak. The hypothalamus extract serves as a source of endothelial cell growth factor. The pH of the cell culture media was 7.4.

After the endothelial cells reach confluency, they are passaged with 0.25% trypsin containing 0.02% EDTA, and subsequent subculturing was performed using the same solution. The cells were exposed to this mixture in Hank's balanced salt solution at room temperature for about 1 minute.

Finally, approximately $2 \times 10^4$ cells/well were seeded in microtiter plates. The endothelial cell nature of the cells was confirmed both by their cobblestone morphology at confluency, and the fact that they stained positive for Factor VIII antigen by indirect immunofluorescence. The latter procedure is well known in the art, and is described by Jaffe, E. A., 1973, *J. Clin. Invest.*, 52:2745.

Monolayers of endothelial cells, prior to the fifth passage, were established on polystyrene, 96-well flat bottom micro titer plates (Corning Corporation) in Medium 199 containing 20% fetal calf serum 25 mM hepes, pH 7.4, and the other supplements described above. The surfaces of the micro titer plates were incubated with 6.4 $\mu$g/ml human plasma fibronectin for 30 minutes at 25° C. prior to plating the endothelial cells. The solution of fibronectin was removed before addition of endothelial cells.

The endothelial cell cultures were used when they were confluent The endothelial cell monolayers were washed with RPMI plus 1% fetal calf serum and incubated with 10 U/ml of IL-1 α to activate the endothelial cells, and 1:10 dilutions of COS cell lysates. Next, labelled monocytes at a final concentration of $5 \times 10^5$ cells per well were added and allowed to settle for 30 minutes onto the endothelial cell monolayers.

Human monocytes were obtained from venus blood from several healthy adult volunteers using an anti-coagulant (10% heparin) followed by centrifugation of the blood on Ficoll-Hypaque gradients. Contaminating erythrocytes were removed by hypotonic lysis. The remaining cell population consisted of 95 to 98% polymorphonuclear leukocytes, and these cells were suspended at a concentration of $50 \times 10^6$ cells per ml in Hank's balanced salt solution, pH 7.4.

The monocytes were labelled with [111]Indium-oxide (100 $\mu$Ci/ $10^8$ PMNs) (10 mCi/mml, Amersham Corp.). Labelling occurred at room temperature in Hank's solution for 15 minutes, after which the labelled cells were isolated by centrifugation for 5 minutes, and to remove residual unincorporated label, washed twice with Hank's balanced salt solution, and then suspended in RPMI supplemented with 1% fetal calf serum.

As mentioned above, $5 \times 10^5$ of the labelled monocytes were added per well in 96-well micro titer plates. Incubations were conducted for 30 minutes at 37° C., in a tissue culture incubator in an atmosphere of 5% $CO_2$, 95% air.

After the 30 minute incubation period, during which the monocytes adhere to the endothelial cell monolayer, the micro titer plates were filled and sealed with adherent transparent plastic (Dynatech, Inc., Alexander, Va.), inverted and centrifuged using a micro plate carrier, obtainable from Beckman Instruments Corp. Centrifugation was at 75×g for 5 minutes at room temperature. This effectively removed nonadherent PMNs from the endothelial cell monolayers. Next, the plates were blotted dry and the number of monocytes that remained adherent to the endothelial cell monolayers was determined using a gamma counter. The results are shown in Table 2, and they are expressed as the percent of monocytes that remained adherent to the endothelial cell monolayers. The experiments were conducted using monocytes isolated from two individuals, donor 1 and donor 2.

TABLE 1

Inhibition of Binding of Human Peripheral Blood Monocytes to IL-1 Stimulated Endothelial Cells

| COS Lysate | Donor 1 | | Donor 2 | |
|---|---|---|---|---|
| | % Binding | % Change | % Binding | % Change |
| Mock | 14.9 | 7 | 17.3 | 5 |
| SRα | 14.1 | 0 | 14.4 | −15 |
| IL-2 | 14.8 | 6 | 17.2 | 4 |
| icIL-1ra (anti-sense) | 14.4 | 3 | 15.7 | −6 |
| icIL-1ra (sense) | 6.9 | −59 | 6.8 | −66 |

The data shown in Table 1 are instructive in several aspects. First, neither COS cell lysates prepared from mock transfected cells, nor lysates prepared from the SRα vector lacking the IL-1 receptor antagonist DNA coding sequence cause a significant or reproducible decrease in monocyte adhesion to the endothelial cell monolayer. Similarly, neither COS cell lysates prepared from cells transfected with IL-2 vector nor plasmid containing IL-1 receptor antagonist DNA in the anti-sense orientation effect the adhesion of monocytes. In contrast, however, lysates prepared from COS cells transfected with icIL-1ra sense DNA reduce the number of monocytes that adhere to the endothelial cell layer by greater than 50% from both donors.

These results convincingly establish that an IL-1 receptor antagonist can reduce the adhesion of monocytes to endothelial cells and thus have positive medical applications as presented in Examples 3 and 4, below.

EXAMPLE 2

Effect of IL-1 Receptor Antagonist on IL-1 Dependent IL-2 Production

To further determine the effectiveness of the IL-1 receptor antagonist to compete with IL-1 for binding to the IL-1 receptor, the capacity of the antagonist to inhibit IL-1 induced production of IL-2 from LBRM-33 1A5 cells was determined. LBRM-33 1A5 cells are known to produce IL-2 in response to IL-1. LBRM-33 is described by Gillis, S. et al., 1981, *PNAS*, 78:1133 and is on deposit with the ATCC with Accession No. CRL 8079. IL-2 levels were measured using a cellular assay involving a cell line that requires IL-2 for survival. The cell line employed was HT-2, and the levels of IL-2 were determined by 3H-thymidine incorporation after an 18–24 hour period. HT-2 cells are a mouse IL-2 dependent cell line which die in the absence of IL-2. The assay is described by Gillis et al., 1978, *J. of Immunol.*, 120:2027.

LBRM-33 cells were induced with 0.08 U/ml IL-1 α, obtained from Cistron Biotechnology, Pine Brook, N.J., plus 2.5 µg/ml PHA, obtained from Sigma Chemical Corporation, St. Louis, Mo., and various dilutions of the COS cell lysates. After 24 hours LBRM-33 cell culture supernatants were tested for IL-2 using the HT-2 cell assay as described by Gillis, et al., above.

TABLE 2

Inhibition of IL-1 Induced IL-2 Production by LBRM-33 Cells

| | % Control HT-2 Proliferation Dilution: | | | | |
|---|---|---|---|---|---|
| COS Lysate | 1:8 | 1:16 | 1:32 | 1:64 | 1:128 |
| Mock | 42 | 70 | 86 | 91 | 86 |
| SRα | 43 | 71 | 88 | 90 | 106 |
| IL-2 | 448 | 456 | 460 | 488 | 373 |
| icIL-1ra (anti-sense) | 38 | 62 | 86 | 85 | 90 |
| icIL-1ra (sense) | 6 | 21 | 46 | 57 | 69 |

It is apparent based on the results shown in Table 2 that lysates prepared from COS cells transfected with icIL-1ra sense DNA inhibit the production of IL-2 from LBRM-33 cells. In contrast, COS cell lysates prepared from mock transfected cells, or cells infected with the vector SRα that did not contain the intracellular IL-1 receptor antagonist DNA coding sequence show no inhibitory effect. Two additional lysate controls were run. COS cells transfected with SRα encoding IL-2 and lysates prepared from cells transfected with plasmid containing IL-1 receptor antagonist DNA in the anti-sense orientation. Neither control caused a significant inhibition of IL-2 production. Note that lysates prepared from COS cells transfected with SRα encoding IL-2 exhibit significant IL-2 levels in the assay. This is because IL-2 is carried over from the IL-2 transfection, and thus produces an apparent positive signal in the HF-2 assay.

The above results clearly establish that the intracellular form of the IL-1 receptor antagonist effectively blocks the IL-1 induced production of IL-2.

EXAMPLE 3

Inhibition of Prostaglandin Production

The effect of the intracellular IL-1 receptor antagonist on prostaglandin production by human fibroblasts was determined. NHDF-194 human fibroblasts were obtained from Clonetics Corporation, San Diego, Calif., and cultured using standard methods. Prostaglandin, specifically prostaglandin $E_2$, was assayed by RIA using a commercial kit available from Dupont Corporation, NEK-020. The results are shown in Table 3.

COS cell lysates were prepared from COS cells that were transfected with the vector, SRα, with the IL-1 receptor antagonist DNA sequence, or containing the sequence in the wrong orientation. Inhibitor and IL-1 were added to the appropriate lysate at a 150 U/ml ($10^6$ U/mg, Cistron Corporation) and incubated with $2 \times 10^4$ fibroblasts for 18 hours, after which cultures supernatants were collected and assayed for prostaglandin $E_2$. Table 3 shows that fibroblasts not exposed to IL-1 do not exhibit elevated levels of prostaglandin, whereas those that were exposed to IL-1 do produce prostaglandin in the range of about 1000 pg/well (0.2 ml). Inhibition of prostaglandin production was observed only with COS cell lysates prepared from COS cells transfected with the intracellular IL-1 receptor antagonist oriented in the correct orientation. The inhibited level observed is about an order of magnitude below either of the controls.

TABLE 3

IcIL-1ra* Blocks IL-1 Induced Fibroblast Prostaglandin Production

| Sample | PGE$_2$ (pg) | |
|---|---|---|
| | No IL-1 | 15 U/ml IL-1 |
| Control | 47–51 | 790–1072 |
| icIL-1ra* | | |
| Correct Orientation | | |
| 1:4 | 58 | 88 |
| 1:8 | 48 | 114 |
| 1:16 | 53 | 157 |
| Wrong Orientation | | |
| 1:4 | 89 | 1700 |
| 1:8 | 62 | 1120 |
| 1:16 | 50 | 990 |

*Intracellular IL-1 Receptor Antagonist

EXAMPLE 4

Prophylactic Use of the Intracellular IL-1 Receptor Antagonist For Reducing Ischemic Injury The intracellular IL-1 receptor antagonist can be used to reduce or prevent ischemic injury as exemplified by the following example. An experimental system with which to test the effectiveness of the intracellular IL-1 receptor antagonist is a rat ligation model. Briefly, this would consist of using rats that weight about 300 grams, anesthetizing them with a suitable anesthetic such as pentabarbial and performing a thoracectomy. Next, the left anterior descending coronary artery would be ligated at its origin, and the ligation maintained for about 1 hour. This effectively reduces or eliminates blood flow thus setting the stage for ischemic injury to the artery. Subsequently, the ligation would be released to allow reperfusion, and the reperfusion permitted to take place for 30 minutes to 1 hour. For the experimental group of animals, reperfusion would be accompanied by administering into the femoral vein appropriate amounts of the intracellular IL-1 receptor antagonist, and this would range from 50 µg/–1000 µg/per kilogram of body weight. The control group would receive a saline solution lacking the receptor antagonist.

Twenty-four hours following reperfusion, the rats would be reanesthetized, the heart removed, and the left ventricles cut parallel to the atrioventricular space sulcus into slices. The tissue slices may be stained at 37° C. for 15 minutes using an appropriate dye, particularly triphenyltetrazolium chloride, and the size of the infarction determined by weighing the tissue.

It would be expected that the size of infarcts in tissue taken from rats that receive the intracellular IL-1 receptor antagonist would be decreased by about 50% compared to tissue removed from control animals.

EXAMPLE 5

IL-1 Receptor Antagonist as a Cancer Therapeutic

IL-1 is an autocrine growth factor for certain cancers. Tsai and Gaffney, 1987, *JNCI*, 79:77–81. Thus, the IL-1 receptor antagonist inhibitor would interfere with the autocrine activity of IL-1 and be an effective chemotherapeutic for the treatment of this form of cancer. The inhibitor can be administered in an effective amount, with the dosage of the inhibitor normally being determined by the prescribing physician. It is to be expected that the dosage will vary according to the tumor type, tumor mass, as well as the age, weight, and response of the individual patient. Typically, the amount of inhibitor administered per dose will be in the range of about 0.1 to 25 mg/kg of body weight, with the preferred dose being about 0.1 to 10 mg/kg of patient body weight. For parenteral administration, the inhibitor will be formulated in an injectable form combined with a pharmaceutically acceptable parenteral vehicle. Such vehicles are well known in the art and examples include water, saline, Ringer's solution, dextrose solution, and solutions consisting of small amounts of the human serum albumin. The vehicle may contain minor amounts of additives that maintain the isotonicity and stability of the inhibitor. The preparation of such solutions is within the skill of the art. Typically, the IL-1 receptor antagonist inhibitor will be formulated in such vehicles at a concentration of about 1–8.0 mg/ml.

EXAMPLE 6

IL-1 Receptor Antagonist as an AIDS Medicament

Figure 2:
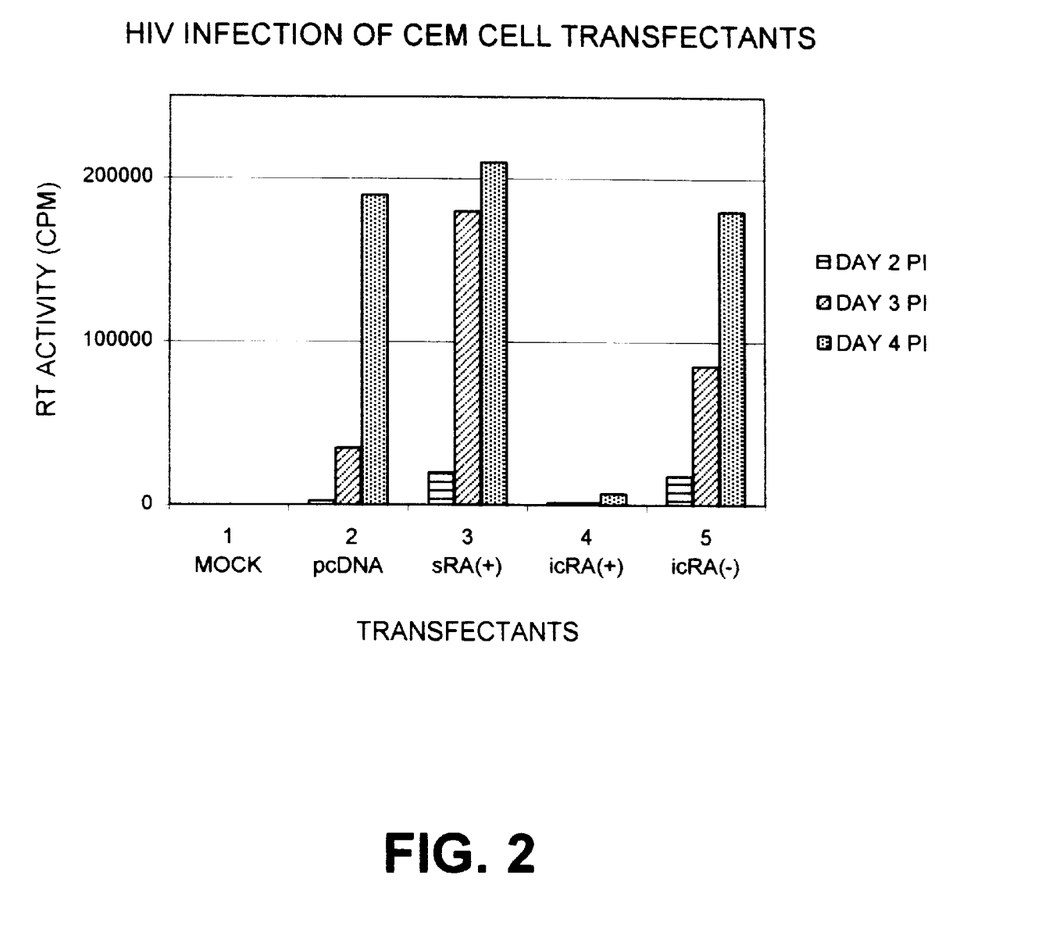
FIG. 2 shows the HIV infection of transfected CEM cells, (i.e., transfected human T cell) as measured by reverse transcriptase (RT) activity (CPM) for (1) non-infected CEM cells ("mock"); (2) CEM cells infected with the empty plasmid ("pcDNA"); (3) CEM T cells transfected to express soluble IL-1 receptor antagonist cDNA in plasmid pcDNA ("sRA(+)"); (4) CEM T cells transfected to express intracellular IL-1 receptor antagonist ("icRA(+)"); and (5) untransfected CEM T cells ("icRA(−)").

Using the materials and methods described above or that are well known in the art, the IL-1 receptor antagonist cDNA (SEQ ID NO: 1) presented in FIG. 1 was transfected into a human T-cell line, CEM, and shown to down regulate the expression of CD4 as revealed by FACS using anti-CD4 antibody. CEM cells transfected with the antagonist had no detectible CD4 on the cell surface, and such cells when exposed to HIV are not infected by virus as revealed by reverse transcriptase activity (FIG. 2). FIG. 2 also shows that the secreted form of the IL-1 receptor antagonist is not effective in blocking HIV infection, and FACS sorting revealed that this molecule does not down regulate CD4 expression.

It is apparent, based on the above results, that the intracellular form of the IL-1 receptor antagonist, or the secreted form without its leader sequence, would be useful to prevent or control HIV infection by removing CD4 positive T-cells from a patient, transfecting the cells with either antagonist, but preferably the intracellular form, and returning the cells to the patient. Such cells would no longer be subject to infection by the virus, and thus significantly extend the life span of the patient.

EXAMPLE 7

Intracellular IL-1 Receptor Antagonist for the Detection of Endometrial Cancer

To determine whether alterationS of IL-1 mediated events by receptor antagonists may further be implicated in the pathogenesis of cancer we studied the expression of IL-1 and IL-1 receptor antagonists in normal endometrium and endometrial cancers. RNA was extracted from 11 benign endometrium and 20 endometrial cancers. mRNA expression of IL-1, secreted (sIL-1ra), and intracellular (icIL-1ra) IL-1 receptor antagonist was determined using reverse transcriptase polymerase chain reaction. IL-1 was expressed by normal endometrium and endometrial cancer, expression did not differ between these two tissue types. sIL-1ra was not expressed by any endometrial sample. However, normal samples showed minimal expression of icIL-1ra while endometrial cancers showed significantly higher levels of expression, up to 100×(p=0.03). Because icIL-1ra transcripts were increased in endometrial cancers, tissue samples were stained with a polyclonal antibody recognizing IL-1 receptor antagonists. Normal endometrium showed epithelial staining and no stromal staining for IL-1ra. In contrast, in endometrial cancers the stromal component stained strongly for IL-1ra. We conclude that icIL-1ra mRNA expression is increased in endometrial cancers and corresponds to increased IL-1ra seen in stromal tissue in neoplasias.

The present invention has been described with reference to specific embodiments. However, this application is intended to cover those changes and substitutions which may be made by those skilled in the art without departing from the spirit and the scope of the appended claims.

We claim:

1. A method for down regulating CD4 expression in a human T cell, the method comprising transforming a human T cell in vitro with a recombinant nucleic acid construct comprising a gene that encodes an intracellular IL-1 receptor antagonist, such gene being operably linked to a promoter, whereby the expression of said gene in said T cell down regulates the expression of CD4 therein.

2. The method of claim 1, wherein said intracellular IL-1 receptor antagonist has the amino acid sequence ID NO: 2.

3. The method of claim 1, wherein the gene that encodes said intracellular IL-1 receptor antagonist has the nucleotide sequence shown in SEQUENCE ID NO: 1.

4. A method for preventing or inhibiting HIV infection in a human T cell, said method comprising transforming a human T cell in vitro with a recombinant nucleic acid construct comprising a gene that encodes an intracellular IL-1 receptor antagonist, said gene being operably linked to a promoter, whereby expression of said gene in said human T cell prevents or inhibits HIV infection of said human T cell.

5. The method of claim 4, wherein said intracellular IL-1 receptor antagonist has the amino acid sequence of SEQUENCE ID NO: 2.

6. The method of claim 4, wherein said gene that encodes an intracellular IL-1 receptor antagonist has the nucleotide sequence shown in SEQUENCE ID NO: 1.

7. A method for down regulating CD4 expression in a human T cell, the method comprising transfecting a human T cell in vitro or ex vivo with a recombinant nucleic acid construct comprising a gene that encodes an intracellular IL-1 receptor antagonist, such gene being operably linked to a promoter, whereby the expression of said gene in said T cell down regulates the expression of CD4 therein.

8. A method for down regulating CD4 expression in a human T cell, the method comprising transfecting a human T cell in vitro or ex vivo with a recombinant nucleic acid construct comprising a gene that encodes an intracellular IL-1 receptor antagonist, such gene being operably linked to a promoter and having a nucleic acid sequence of SEQ ID NO: 1, whereby the expression of said gene in said T cell down regulates the expression of CD4 therein.

9. A method for down regulating CD4 expression in a human T cell, the method comprising transfecting a human T cell in vitro or ex vivo with a recombinant nucleic acid construct comprising a gene that encodes an intracellular IL-1 receptor antagonist of SEQ ID NO: 2, such gene being operably linked to a promoter, whereby the expression of said gene in said T cell down regulates the expression of CD4 therein.

* * * * *

UNITED STATES PATENT AND TRADEMARK OFFICE
CERTIFICATE OF CORRECTION

PATENT NO. : 6,087,178
DATED : July 11, 2000
INVENTOR(S) : Haskill et al.

It is certified that error appears in the above-identified patent and that said Letters Patent are hereby corrected as shown below:

On the face of the patent at "[73]' after "Chiron Corporation, Emeryville, Calif.", please add --University of North Carolina at Chapel Hill, Chapel Hill, NC--

Signed and Sealed this

Twenty-second Day of May, 2001

Attest:

NICHOLAS P. GODICI

Attesting Officer  Acting Director of the United States Patent and Trademark Office

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 603 base pairs
        (B) TYPE: nucleic acid
        (C) STRANDEDNESS: single
        (D) TOPOLOGY: linear     (ii) MOLECULE TYPE:

(ix) FEATURE:
        (A) NAME/KEY: CDS
        (B) LOCATION: 124..600

(xi) SEQUENCE DESCRIPTION: SEQ ID NO:1:

```
AGCTCCACCC TGGGAGGGAC TGTGGCCCAG GTACTGCCCG GGTGCTACTT TATGGGCAGC      60

AGCTCAGTTG AGTTAGAGTC TGGAAGACCT CAGANAGACC TCCTGTCCTA TGAGGCCCTC     120

CCC ATG GCT TTA GAG ACG ATC TGC CGA CCC TCT GGG AGA AAA TCC AGC      168
    Met Ala Leu Glu Thr Ile Cys Arg Pro Ser Gly Arg Lys Ser Ser
    1               5                  10                  15

AAG ATG CAA GCC TTC AGA ATC TGG GAT GTT AAC CAG AAG ACC TTC TAT      216
Lys Met Gln Ala Phe Arg Ile Trp Asp Val Asn Gln Lys Thr Phe Tyr
                20                  25                  30

CTG AGG AAC AAC CAA CTA GTT GCT GGA TAC TTG CAA GGA CCA AAT GTC      264
Leu Arg Asn Asn Gln Leu Val Ala Gly Tyr Leu Gln Gly Pro Asn Val
            35                  40                  45

AAT TTA GAA GAA AAG ATA GAT GTG GTA CCC ATT GAG CCT CAT GCT CTG      312
Asn Leu Glu Glu Lys Ile Asp Val Val Pro Ile Glu Pro His Ala Leu
        50                  55                  60

TTC TTG GGA ATC CAT GGA GGG AAG ATG TGC CTG TCC TGT GTC AAG TCT      360
Phe Leu Gly Ile His Gly Gly Lys Met Cys Leu Ser Cys Val Lys Ser
    65                  70                  75

GGT GAT GAG ACC AGA CTC CAG CTG GAG GCA GTT AAC ATC ACT GAC CTG      408
Gly Asp Glu Thr Arg Leu Gln Leu Glu Ala Val Asn Ile Thr Asp Leu
80                  85                  90                  95

AGC GAG AAC AGA AAG CAG GAC AAG CGC TTC GCC TTC ATC CGC TCA GAC      456
Ser Glu Asn Arg Lys Gln Asp Lys Arg Phe Ala Phe Ile Arg Ser Asp
                100                 105                 110

AGT GGC CCC ACC ACC AGT TTT GAG TCT GCC GCC TGC CCC GGT TGG TTC      504
Ser Gly Pro Thr Thr Ser Phe Glu Ser Ala Ala Cys Pro Gly Trp Phe
            115                 120                 125

CTC TGC ACA GCG ATG GAA GCT GAC CAG CCC GTC AGC CTC ACC AAT ATG      552
Leu Cys Thr Ala Met Glu Ala Asp Gln Pro Val Ser Leu Thr Asn Met
        130                 135                 140

CCT GAC GAA GGC GTC ATG GTC ACC AAA TTC TAC TTC CAG GAG GAC GAG      600
Pro Asp Glu Gly Val Met Val Thr Lys Phe Tyr Phe Gln Glu Asp Glu
    145                 150                 155
```

-continued

```
TAG                                                          603
```

(2) INFORMATION FOR SEQ ID NO:2:

(i) SEQUENCE CHARACTERISTICS:
        (A) LENGTH: 159 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Ala Leu Glu Thr Ile Cys Arg Pro Ser Gly Arg Lys Ser Ser Lys
 1               5                  10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
            85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
            115                 120                 125

Cys Thr Ala Met Glu Ala Asp Gln Pro Val Ser Leu Thr Asn Met Pro
130                 135                 140

Asp Glu Gly Val Met Val Thr Lys Phe Tyr Phe Gln Glu Asp Glu
145                 150                 155
```